US00PP35447P2

(12) United States Plant Patent
de Vos

(10) Patent No.: US PP35,447 P2
(45) Date of Patent: Oct. 31, 2023

(54) ***HYDRANGEA* PLANT NAMED 'HYLV17522'**

(50) Latin Name: *Hydrangea paniculata*
Varietal Denomination: HYLV17522

(71) Applicant: KWEKERIJ LENDERT de VOS B.V., Reeuwijk (NL)

(72) Inventor: Lendert de Vos, Reeuwijk (NL)

(73) Assignee: KWEKERIF LENDERT de VOS B.V, Reeuwijk (NL)

( * ) Notice: Subject to any disclaimer, the term of this patent is extended or adjusted under 35 U.S.C. 154(b) by 0 days.

(21) Appl. No.: 18/101,575

(22) Filed: Jan. 25, 2023

Related U.S. Application Data

(60) Provisional application No. 63/321,096, filed on Mar. 17, 2022.

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 5/02; A01H 5/00
See application file for complete search history.

*Primary Examiner* — Kent L Bell
(74) *Attorney, Agent, or Firm* — C. Anne Whealy

(57) ABSTRACT

A new and distinct cultivar of *Hydrangea* plant named 'HYLV17522', characterized by its relatively compact, upright to broadly spreading and mounding plant habit; moderately vigorous growth habit; freely branching habit; strong and sturdy stems; freely flowering habit; panicles with yellowish green-colored sterile flowers that become dark red in color with subsequent development; and good garden performance.

2 Drawing Sheets

Botanical designation: *Hydrangea paniculata.*
Cultivar denomination: 'HYLV17522'.

An European Community Plant Breeder's Rights application for this plant was filed by the Applicant/Assignee of the instant application, Kwekerij Lendert de Vos of Reeuwijk, The Netherlands on Sep. 24, 2021, application number 2021/2376. Foreign priority is not claimed to this European Plant Breeder's Rights application.

BACKGROUND OF THE INVENTION

The present invention relates to a new and distinct cultivar of *Hydrangea* plant, botanically known as *Hydrangea paniculata*, commercially referred to as a Paniculated *Hydrangea* and hereinafter referred to by the name 'HYLV17522'.

The new *Hydrangea* plant is a product of a planned breeding program conducted by the Inventor in Reeuwijk, The Netherlands. The objective of the breeding program is to create new compact and strong *Hydrangea* plants with attractive inflorescences and good postproduction longevity.

The new *Hydrangea* plant originated from an open-pollination during the summer of 2015 of a proprietary selection of *Hydrangea paniculata* identified as code number P13502, not patented, as the female, or seed, parent with an unknown selection of *Hydrangea paniculata* as the male, or pollen, parent. The new *Hydrangea* plant was discovered and selected as a single flowering plant from within the progeny of the stated open-pollination in a controlled greenhouse environment in Reeuwijk, The Netherlands in August, 2017.

Asexual reproduction of the new *Hydrangea* plant by terminal vegetative cuttings since August, 2017 in a controlled greenhouse environment in Reeuwijk, The Netherlands has shown that the unique features of this new *Hydrangea* plant are stable and reproduced true to type in successive generations of asexual reproduction.

SUMMARY OF THE NEW PLANT

Plants of the new *Hydrangea* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'HYLV17522'. These characteristics in combination distinguish 'HYLV17522' as a new and distinct *Hydrangea* plant:

1. Relatively compact, upright to broadly spreading and mounding plant habit.
2. Moderately vigorous growth habit.
3. Freely branching habit.
4. Strong and sturdy stems.
5 Freely flowering habit.
6. Panicles with yellowish green-colored sterile flowers that become dark red in color with subsequent development.
7. Good garden performance.

Plants of the new *Hydrangea* can be compared to plants of the female parent selection. Plants of the new *Hydrangea* differ primarily from plants of the female parent selection in the following characteristics:

1. Inflorescences of plants of the new *Hydrangea* are taller and more conical in shape than inflorescences of plants of the female parent selection.
2. Sterile flowers of plants of the new *Hydrangea* are yellowish green in color becoming dark red at the end of the flowering season whereas sterile flowers of plants of the female parent selection are white in color.

Plants of the new *Hydrangea* can be compared to plants of *Hydrangea paniculata* 'HYLV17520', disclosed in U.S. Plant patent application Ser. No. 18/101,574 filed concurrently. In side-by-side comparisons, plants of the new *Hydrangea* differ primarily from plants of 'HYLV17520' in the following characteristics:

1. Plants of the new *Hydrangea* are taller and somewhat more outwardly spreading than plants of 'HYLV17520'.
2. Plants of the new *Hydrangea* have longer leaves than plants of 'HYLV17520'.
3. Inflorescences of plants of the new *Hydrangea* are taller and narrower than inflorescences of plants of 'HYLV17520'.
4. Inflorescences of plants of the new *Hydrangea* have more sterile flowers than inflorescences of plants of 'HYLV17520'.

Plants of the new *Hydrangea* can also be compared to plants of *Hydrangea paniculata* 'Diamant Rouge', not patented. In side-by-side comparisons, plants of the new *Hydrangea* differ primarily from plants of 'Diamant Rouge' in the following characteristics:

1. Plants of the new *Hydrangea* are more compact and shorter than plants of 'Diamant Rouge'.
2. Plants of the new *Hydrangea* are denser and have stronger and sturdier stems than plants of 'Diamant Rouge'.
3. Inflorescences of plants of the new *Hydrangea* are denser and more uniform in shape than inflorescences of plants of 'Diamant Rouge'.
4. Inflorescences of plants of the new *Hydrangea* have smaller sterile flowers than inflorescences of plants of 'Diamant Rouge'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

DETAILED BOTANICAL DESCRIPTION

Figure 2:
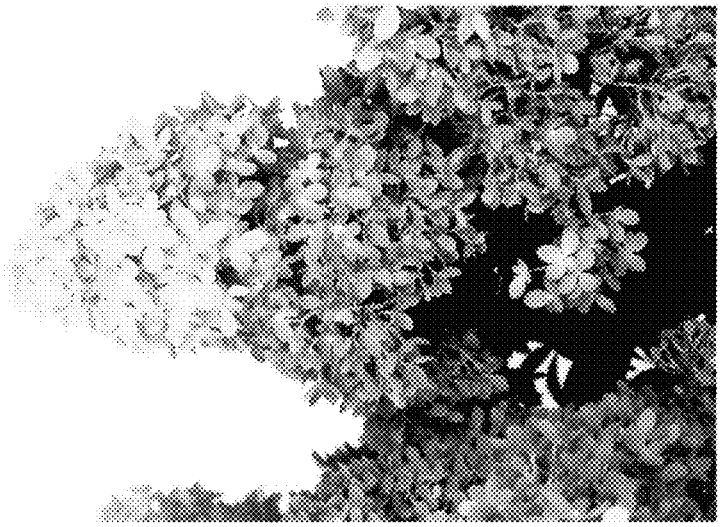
FIG. 2 is a close-up view of typical inflorescences of 'HYLV17522'.
Figure 1:
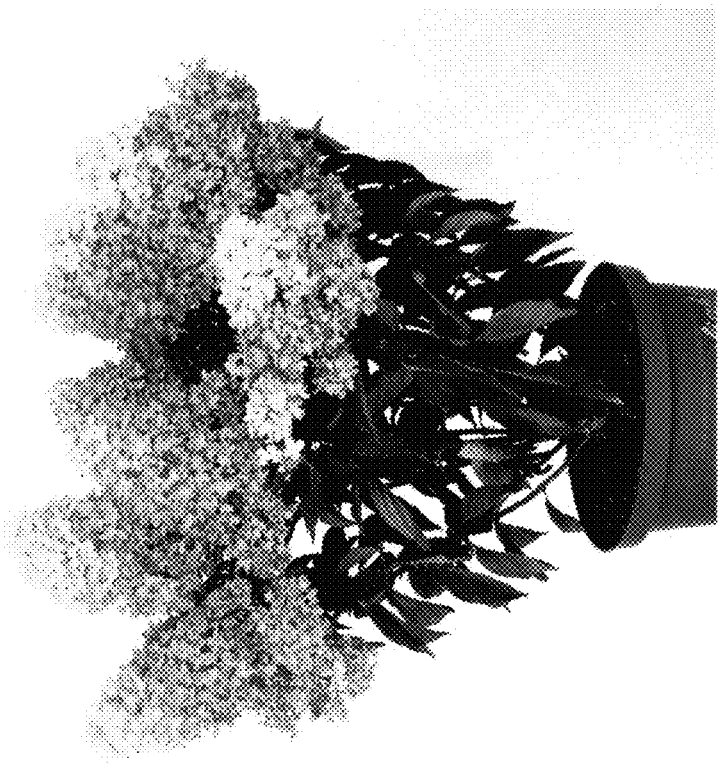
FIG. 1 is a side perspective view of a typical flowering plant of 'HYLV17522' grown in a container.
Figure 3:
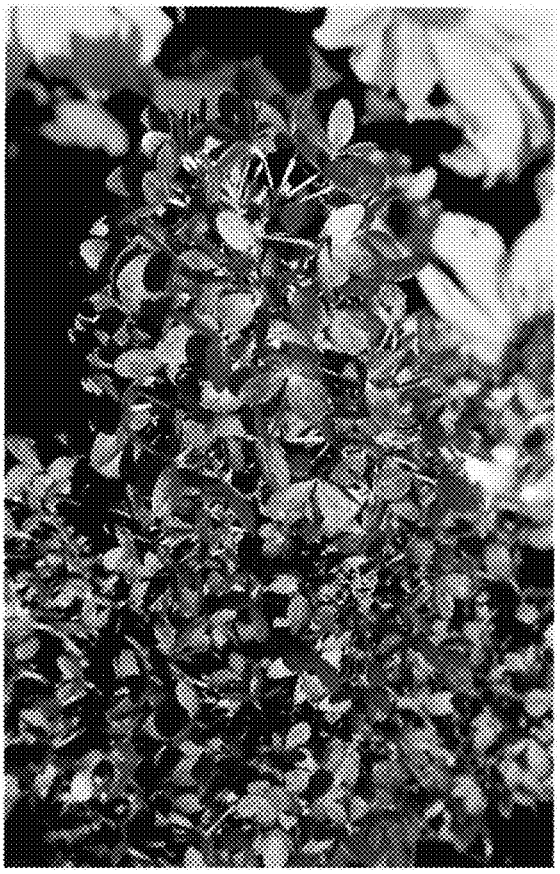
FIG. 3 is a close-up view of typical inflorescences of 'HYLV17522' at the end of the flowering season.
Figure 4:
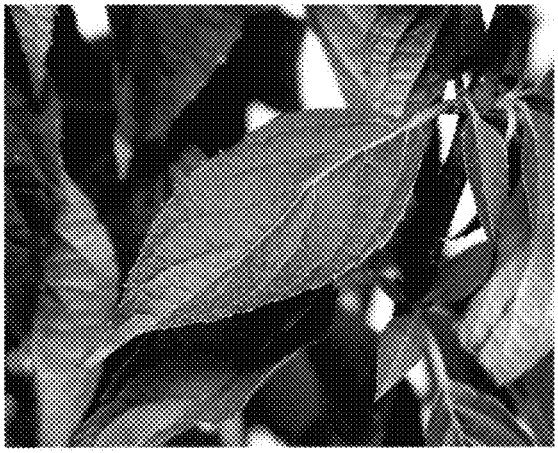
FIG. 4 is a close-up view of typical leaves of 'HYLV17522'.

Plants used in the aforementioned photographs and in the following description were grown during the summer in 21-cm containers in an outdoor nursery in Reeuwijk, The Netherlands and under cultural practices typical of commercial *Hydrangea* production. During the production of the plants, day temperatures ranged from 18° C. to 30° C., night temperatures ranged from 8° C. to 18° C. Plants of the new *Hydrangea* were pinched in the early summer. Plants were three years old when the photographs and description were taken. In the following description, color references are made to The Royal Horticultural Society Colour Chart, 2015 Edition, except where general terms of ordinary dictionary significance are used. Paniculated *Hydrangea* plants are not typically treated with aluminum sulfate to "blue" the flower color.

Botanical description: *Hydrangea paniculata* 'HYLV17522'.

Parentage:

*Female, or seed, patent*.—Proprietary selection of *Hydrangea paniculata* identified as code number P13502, not patented.

*Male, or pollen, patent*.—Unknown selection of *Hydrangea paniculata*, not patented.

Propagation:

*Type cutting*.—By vegetative terminal cuttings.

*Time to initiate roots, summer*.—About 16 days at temperatures ranging from 20° C. to 30° C.

*Time to produce a rooted young plant, summer*.—About four months at temperatures ranging from 20° C. to 30° C.

*Root description*.—Medium in thickness to thick; fibrous; typically light brown in color, actual color of the roots is dependent on substrate composition, water quality, fertilizer type and formulation, substrate temperature and physiological age of roots.

*Rooting habit*.—Freely branching; dense.

Plant description:

*Plant and growth habit*.—Relatively compact; upright to broadly outwardly spreading and mounding plant habit; flattened broadly obovate in overall shape; strong and sturdy stems; moderately vigorous growth habit and moderate growth rate; about one year from propagation are required to produce small finished plants.

*Plant height*.—About 55 cm.

*Plant diameter or area of spread*.—About 55.5 cm.

Lateral branch description:

*Branching habit*.—Freely branching habit with about eleven lateral branches developing per plant; pinching is not required, but will enhance lateral branch development.

*Length*.—About 31.1 cm.

*Diameter*.—About 6 mm.

*Internode length*.—About 4.5 cm.

*Strength*.—Strong, sturdy.

*Aspect*.—Erect to about 65° from vertical.

*Texture*.—Sparsely pubescent; becoming woody with subsequent development.

*Color, developing*.—Close to 146B.

*Color, fully developed*.—Close to N199A; when woody, close to 197D and 199B to 199D.

*Lenticels*.—Density: Medium density. Length: About 1 mm. Diameter: About 0.5 mm. Color: Close to 164C.

Leaf description:

*Arrangement*.—Opposite or in whorls of three, simple.

*Length*.—About 8.6 cm.

*Width*.—About 4.6 cm.

*Shape*.—Ovate; slightly to moderately carinate.

*Apex*.—Apiculate to acute.

*Base*.—Obtuse.

*Margin*.—Serrate.

*Texture and luster, upper and lower surfaces*.—Sparsely pubescent; matte.

*Venation pattern*.—Pinnate.

*Color*.—Developing leaves, upper surface: Close to 143A. Developing leaves, lower surface: Close to a blend of 144A and 146B. Fully developed leaves, upper surface: Close to NN137B; venation, close to N170C. Fully developed leaves, lower surface: Close to 147B; venation, close to 146C.

*Petioles*.—Length: About 1.6 cm. Diameter: About 2.5 mm. Texture and luster, upper surface: Smooth, glabrous; slightly glossy. Texture and luster, lower surface: Sparsely pubescent; slightly glossy. Color, upper surface: Close to 146C. Color, lower surface: Close to 144A.

Flower description:

*Flower type and habit*.—Showy rotate sterile flowers and small, inconspicuous rotate fertile flowers arranged on terminal panicles; panicles irregular conical in shape; sterile flowers face upright, outwardly to slightly drooping and fertile flowers face mostly upright.

*Fragrance*.—Faintly fragrant; sweet and pleasant.

*Natural flowering season*.—In the garden, plants flower continuously from the midsummer to late summer in The Netherlands.

*Flower longevity*.—Good postproduction longevity; sterile flowers maintain good substance for about six weeks on the plant, sterile flowers persistent; fertile flowers last for about five days on the plant, fertile flowers not persistent.

*Quantity of flowers*.—Freely flowering habit; about 1,000 sterile flowers per panicle and about 400 fertile flowers per panicle.

*Panicle height*.—About 20.4 cm.

*Panicle diameter*.—About 15.9 cm.

*Panicle peduncles*.—Length: About 19 cm. Diameter: About 3.5 mm. Strength: Moderately strong. Aspect: Primary peduncles, mostly erect; lateral peduncles, about 40° from primary peduncle axis. Texture and luster: Moderately pubescent; matte. Color: Close to 146B to 146C.

*Sterile flower buds*.—Length: About 5 mm. Diameter: About 1.5 cm. Shape: Broadly cup-shaped. Color: Close to 145B and 145C.

*Fertile flower buds*.—Length: About 3 mm. Diameter: About 2 mm. Shape: Broadly obovate. Color: Immature corolla, close to 157D and immature calyx, close to 145B.

*Sterile flower diameter*.—About 2.2 cm.

*Sterile flower depth* (*height*).—About 6 mm.

*Fertile flower diameter*.—About 7 mm.

*Fertile flower depth* (*height*).—About 4 mm.

*Petals, sterile flowers*.—Quantity and arrangement: Three or four in a single whorl. Length: About 3 mm. Width: About 1.25 mm. Shape: Ovate. Apex: Acute. Base: Cuneate. Margin: Entire. Texture and luster, upper and lower surfaces: Smooth, glabrous; slightly glossy. Color: When opening and fully opened, upper surface: Close to NN155D; color does not change with subsequent development. When opening and fully opened, lower surface: Close to NN155D; color does not change with subsequent development.

*Petals, fertile flowers*.—Quantity and arrangement: Five in a single whorl. Length: About 2.5 mm. Width: About 1.25 mm. Shape: Ovate, slightly concave. Apex: Acute. Base: Cuneate. Margin: Entire. Texture and luster, upper and lower surfaces: Smooth, glabrous; slightly glossy. Color: When opening and fully opened, upper surface: Close to NN155B; color does not change with subsequent development. When opening and fully opened, lower surface: Close to NN155B; color does not change with subsequent development.

*Sepals, sterile flowers*.—Quantity and arrangement: Typically four, or occasionally three, arranged in a single whorl. Length: About 1.15 cm. Width: About 7 mm. Shape: Elliptic to slightly obovate. Apex: Obtuse. Base: Cuneate. Margin: Entire. Texture and luster, upper and lower surfaces: Smooth, glabrous; matte. Color: When opening, upper and lower surfaces: Close to 145C. Fully opened, upper surface: Close to 145B; with subsequent development, color becoming closer to 145A and eventually, close to 60A. Fully opened, lower surface: Close to a blend of 145B and 149D; with subsequent development, color becoming closer to a blend of 145A and 146D and eventually, close to 185B.

*Sepals, fertile flowers*.—Quantity and arrangement: Five in a single whorl. Length: About 1 mm. Width: About 1 mm. Shape: Deltoid. Apex: Broadly acuminate. Base: Broadly cuneate. Margin: Entire. Texture and luster, upper and lower surfaces: Smooth, glabrous; matte. Color: When opening and fully opened, upper surface: Close to 145C; color does not change with subsequent development. When opening and fully opened, lower surface: Close to 145C; color does not change with subsequent development.

*Pedicels, sterile flowers*.—Length: About 1.1 cm. Diameter: About 1 mm. Strength: Moderately strong. Aspect: About 30° from main peduncle axis Texture and luster: Moderately pubescent; matte. Color: Close to 145D.

*Pedicels, fertile flowers*.—Length: About 1.5 mm. Diameter: About 0.75 mm. Strength: Moderately strong. Aspect: About 5° from vertical. Texture and luster: Moderately pubescent; matte. Color: Close to 145C to 145D with one or two small spots, close to 185B.

*Reproductive organs, sterile flowers*.—Stamens: Quantity per flower: Eight. Filament length: About 1 mm. Filament color: Close to NN155A. Anther shape: Oblong. Anther length: About 0.5 mm. Anther color: Close to 158D to lighter than 158D. Pollen amount: Sparse. Pollen color: Close to lighter than 156D. Pistils: Pistil quantity per flower: One. Pistil length: About 1.5 mm. Stigma shape: Club-shaped. Stigma color: Close to 155C. Style length: About 1.25 mm. Style color: Close to NN155A.

*Reproductive organs, fertile flowers*.—Stamens: Quantity per flower: Ten. Filament length: About 2 mm. Filament color: Close to NN155B. Anther shape: Oblong. Anther length: About 0.5 mm. Anther color: Close to 158D to lighter than 158D. Pollen amount: Sparse. Pollen color: Close to lighter than 156D. Pistils: Pistil quantity per flower: Two or occasionally, three. Pistil length: About 2 mm. Stigma shape: Club-shaped. Stigma color: Close to 155C. Style length: About 1.5 mm. Style color: Close to NN155A. Ovary color: Close to 157A.

*Seeds*.—To date, seed development has not been observed on plants of the new *Hydrangea*.

Pathogen & pest resistance: Plants of the new *Hydrangea* have not been observed to be resistant to pathogens and pests common to *Hydrangea* plants.

Temperature tolerance: Plants of the new *Hydrangea* have been shown to be suitable for USDA Hardiness Zones 5 through 9.

It is claimed:

1. A new and distinct *Hydrangea* plant named 'HYLV17522' as illustrated and described.

* * * * *